United States Patent [19]

Coude et al.

[11] Patent Number: 5,270,320

[45] Date of Patent: Dec. 14, 1993

[54] USE OF A 1-(2-NAPHTHYLETHYL)-4-(3-TRI-FLUOROMETHYLPHENYL)-1,2,3,6-TET-RAHYDROPYRIDINE FOR THE MANUFACTURE OF A MEDICAMENT FOR THE TREATMENT OF CEREBRAL AND NEURONAL DISEASES

[75] Inventors: Francois X. Coude, Toulouse; Jacqueline Fournier, Plaisance du Touch, both of France; Umberto Guzzi, Milan, Italy

[73] Assignee: Elf Sanofi, Paris, France

[21] Appl. No.: 789,044

[22] Filed: Nov. 7, 1991

[30] Foreign Application Priority Data

May 22, 1990 [FR] France ............................ 90 06399

[51] Int. Cl.⁵ ............................................ A61K 31/435
[52] U.S. Cl. ..................................................... 514/277
[58] Field of Search ......................................... 514/277

[56] References Cited

U.S. PATENT DOCUMENTS 5,026,716  6/1991  Bianchetti et al. .................. 514/277

Primary Examiner—Jerome D. Goldberg
Attorney, Agent, or Firm—Bacon & Thomas

[57] ABSTRACT

The invention concerns the use of i.a. 1-[2-(2-naphthyl)ethyl]-4-(3-trifluoromethylphenyl)-1,2,3,6-tetrahydropyridine and its pharmaceutically acceptable addition salts for the preparation of medicaments suitable for the treatment and/or prophylaxis of neuronal degenerative processes including senile dementia, vascular dementia, and Alzheimer's disease.

4 Claims, No Drawings

USE OF A 1-(2-NAPHTHYLETHYL)-4-(3-TRIFLUOROMETHYLPHENYL)-1,2,3,6-TETRAHYDROPYRIDINE FOR THE MANUFACTURE OF A MEDICAMENT FOR THE TREATMENT OF CEREBRAL AND NEURONAL DISEASES

The present invention concerns the use of a 1-(2-naphthylethyl)-4-(3-trifluoromethylphenyl)-1,2,3,6-tetrahydropyridine of the following formula

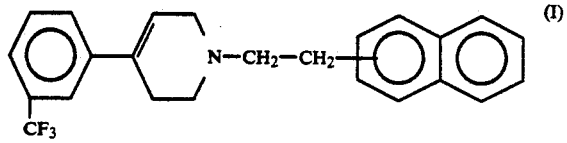

or of a pharmaceutically acceptable salt thereof for the manufacture of a medicament for the treatment and prophylaxis of cerebral and neuronal diseases. More particularly, the present invention concerns the use of a compound of formula (I) or of a pharmaceutically acceptable salt thereof for the manufacture of medicaments suitable for the treatment of diseases associated with neuronal degeneration.

The above formula (I) includes 1-[2-(1-naphthyl)ethyl]- and 1-[2-(2-naphthyl)ethyl]-4-(3-trifluoromethylphenyl)-1,2,3,6-tetrahydropyridines; however, particularly preferred compounds for use in the practice of the present invention are 1-[2-(2-naphthyl)ethyl]-4-(3-trifluoromethylphenyl)-1,2,3,6-tetrahydropyridine and pharmaceutically acceptable salts thereof.

The compounds of formula (I), as free bases or acid addition salts thereof, as well as their preparation, have been described in EP-A-101381.

The nature of the salt is not critical provided it is pharmaceutically acceptable and acids which may be employed to form such salts are of course well known to those skilled in the art.

Examples of acids which may be employed to form pharmaceutically acceptable acid addition salts include such inorganic acids as hydrochloric acid, hydrobromic acid, phosphoric acid, and sulphuric acid and such organic acids as acetic acid, formic acid, propionic acid, benzoic acid, maleic acid, succinic acid, tartaric acid, fumaric acid, citric acid, glyoxylic acid, aspartic acid, methanesulfonic acid, ethanesulfonic acid, benzenesulfonic acid, p-toluene sulfonic acid and the like acids.

In the above European patent application, the compounds are described as anorexigenic agents.

It has now unexpectedly been found that the compounds of formula (I) do exert neurotrophic effects in the nervous system, similar to those of NGF (Nerve Growth Factor) and restore functioning of the nerve cells which are damaged or present anomalies in their physiological role. Said neurotrophic effects have been demonstrated at first by means of a neuritogenesis test in vitro.

IN VITRO PHARMACOLOGICAL EVALUATION

This test has been carried out on isolated nerve cells which are obtained from dissections of the septal region of rat embryos by conventional procedures which afford enriched neuronal suspensions (from 95 to 98%) (S. E. Bottenstein: "Growth and differenciation of neural cells in defined media" in Cell Culture in the Neuroscience, p.3–43, 1985, Ed. S. E. Bottenstein, G. Sato).

More particularly, the septal region of 17-day-old rat embryos has been removed by means of a dissection microscope while keeping said brain tissue at 4° C. in the following medium DME/F-12 containing (v/v)
5% glucose
1% amphotericin B
0.5% gentamycin.

The cells are dissociated by treatment with trypsin-.EDTA at 37° C. for 20 minutes, followed by two centrifugations and washing with PBS. Dissociation is then completed by resuspending the cells in Hanks' solution and gently pipetting the cell suspension to break up the clumps. This step is followed by three centrifugations and the obtained pellet in then resuspended in a serum-supplemented medium:

DME/F-12 containing (v/v)
5% foetal calf serum
5% horse serum
0.1% glutamine
1% amphotericin B
0.5% glutamycin
34 mM KCl.

The obtained cell suspension is poured into a culture flask and kept in the oven at 37° C. under 5% $CO_2$ for 90 minutes. Non-neuronal cells soon stick to the plastic walls of the flask, thus affording a suspension enriched in neurons (95 to 98%). The thus obtained suspension is centrifuged and the pellets are taken up in a serum-free medium (H. W. Muller and N. Seifert, J. Neurosc Res., 8, 195–204, 1982):

DME/F-12 containing (v:v)
1 µg/ml transferrin
3 mM triiodothyronine
5 µg/ml insulin
20 µM hydrocortisone
0.1% glutamine
1% amphotericin B
0.5% gentamycin.

Neurons are plated on to 96 well plates ($5 \times 10^4$ viable cells per well).

Each well is treated with poly-L-Lysine (10 µg/ml) in order to form a matrix which is necessary to neuronal adhesion, survival and differentiation. Aliquots (130 µl) of serumfree medium containing either suitably selected doses of the test compounds of formula (I) or the corresponding concentrations of the solvent employed (dimethylsulfoxide) are distributed in the wells. After depositing the neuronal cells in the wells, the plates are maintained in the oven at 37° C. and 5% $CO_2$ atmosphere for 18 hours. After glutaraldehyde/paraformaldehyde fixation, the cells in the cultures are counted as follows:

for a predetermined microscopic field in each well, the total number of cells is counted as well as the number of cells having at least one neurite (neurite=outgrowth) longer than twice the cell diameter, five fields for each well are counted and for each dose of test compound two wells are incubated, thus obtaining ten data for each dose, the results are expressed as percentage of cells with neurites relative to total surviving neurons. Each group is compared to its control by means of non-parametric Krushall-Wallis analysis.

The results obtained with 1-[2-(2-naphthyl)ethyl]-4-(3-trifluoromethylphenyl)-1,2,3,6-tetrahydropyridine hydrochloride (Compound A) are summarised in following Table I

TABLE I

| Compound - dose | percentage of cells with neurites |
|---|---|
| Compound A - 2.4 nM | 44.8 ± 3.45 |
| Control (DMSO $10^{-6}$) | 30.2 ± 1.68 |
| Compound A - 24 nM | 39.2 ± 2.39 |
| Control (DMSO $10^{-5}$) | 29.4 ± 1.64 |
| Compound A - 240 nM | 44.1 ± 2.02 |
| Control (DMSO $10^{-4}$) | 34.3 ± 1.82 |

NGF in the same test, gave the following results:

|  | percentage of cells with neurites. |
|---|---|
| NGF - 1.6 nM | 51.7 ± 1.61 |
| Control | 40.6 ± 2.08 |

The mechanism through which Compound A elicits said neurotrophic effects has not been cleared up. Anyway it may be excluded that a serotoninergic effect is involved because Compound A has no affinity for serotonine receptors others than 5-HT$_{1A}$ (i.e. 5-HT$_{1C}$; 5-HT$_{1D}$; 5-HT$_2$; 5-HT$_3$) and compounds known as 5-HT$_{1A}$ agonists or partial agonists, including buspirone, ipsapirone, and 8-hydroxy-2-(di-n-propylamino)tetralin (8OH-DPAT) showed to be completely inactives in the above test.

Compound A also is very active (at concentrations ranging from 250 µM to 2.5 µM) in affording survival of neuronal cells in a very poor medium free from growth factors.

IN VIVO PHARMACOLOGICAL EVALUATION

To confirm the significance of the above in vitro positive results, a new experimental model has been set up which allows the in vivo assessment of the neurotrophic/neuroprotectant activity of the compounds of formula (I) in neuronal degenerative processes.

An experimental model for this type of evaluation has recently been proposed by Y. Nakagawa et al (Brain Research, 1987, 408, 57–64).

In the study conducted by these Authors, the resemblance between the neurochemical and Behavioural modifications caused by infusion of a neurotoxicant, in particular colchicine, in the hippocampus and those observed in patients affected by Alzheimer's disease has been clearly pointed out. On the basis of the results published by Y. Nakagawa et al. and bearing in mind the crucial role played by the hippocampus in memory and learning, it has been attempted to set up an experimental model for the Alzheimer's disease of improved feasibility and even closer to the physiopathologies documented in patients with Alzheimer's disease.

The experimental model which is herein provided complies with these requirements: good feasibility and irreversible lesions highly specific for the septohippocampal cholinergic system.

In particular, lesions of the septal neurons have been caused by local injection of vincristine known to be a tubuline polymerisation inhibitor.

With respect to other similar compounds (colchicine and vinblastine) and different injections sites (intraventricular and intrahippocampal) which have been tested, optimum results, both in terms of specific blockade of septohippocampal cholinergic transmission and irreversible lesions, have been obtained.

OPERATIVE PROCEDURES

The animals (male Sprague-Dawley rats weighing about 250 g) are anesthetised with pentobarbital (10 mg/kg i.p.) and placed in a stereotaxic apparatus.

The injection in the medial septum is made at the following coordinates which are calculated according to the atlas of Paxinos and Watson:

A.: 8.9
L.; 0
H.; 6.4 wherein point O corresponds to lambda.

Vincristine is dissolved in artificial cephalorachidian liquid (ACSF) having the following composition NaCl: 150 mM
CaCl$_2$: 1.8 mM
MgSO$_4$: 1.2 mM
K$_2$HPO$_4$: 2 mM
glucose: 10 mM
pH 7.4 at a concentration of 0.6 µmole of vincristine per ml. 1 µl of this solution (0.6 nmole of vincristine) is locally injected in the medial septum over 1 minute.

ASSESSMENT OF THE LESIONS

Evaluation of morphological changes (histoenzymatic AChE determination)

The animals are perfused with a fixating mixture (glutaraldehyde/paraformaldehyde) via the aorta, with a perfusion flow of 25 ml/min for 5 minutes. Brains are removed, fixation being continued for 1 hour, then washed and cryoprotected with 20% sucrose in phosphate buffer. Brains are there cut on a cryostat and the cryostat sections (30 µm thick) of the septum and the hippocampus are mounted on metal slides which are incubated for about 15 hours in the following medium:

| 200 ml of a stock solution | distilled water 925 ml |
|---|---|
|  | CuSO$_4$ 781 mg |
|  | glycine 750 mg |
|  | sodium acetate 2.89 g |
| to which acetylcholine iodide | 230 mg and |
| ethopropazine | 10 mg |
| are added just before use. |  |

The reaction is then detected by means of 2% ammonium sulfide and evidenced by 0.25% AgNO$_3$.

The presence of acetylcholinesterase (generally associated with cholinergic synapses) is indicated as a dark precipitate.

BIOCHEMICAL OBSERVATIONS (ChAT)

ChAT activity is determined by the method described by fonnum (J. Neurochem. 24, 1975, 407–409). Tissue samples are homogenised at 4° C. Each sample is brought to a concentration of 1 mg of protein per ml. Aliquots of the obtained homogenates (10 µl) are incubated for 7'30" at 37° C., in the presence of choline (1.5 mM), acetylCoA (70 µM), $^{14}$C-acetylCoA (30 µM) and physostigmine (0.15 mM). The reaction is stopped by lowering the temperature by means of an ice-bath and adding phosphate buffer (5 ml). After addition of tetraphenylboron/acetone (2 ml) and of a scintillating agent (5 ml), $^{14}$C-acetylcholine is counted in a scintillation spectrometer. Each sample is tested in triplicate.

Each time the result is compared with that obtained with the corresponding control by the Student test.

BEHAVIOURAL STUDIES

Groups of animals kept with an inverse light-dark cycle have been employed specifically for these studies. The rats used in these tests are Winstar rats lesioned as described above.

SOCIAL MEMORY TEST (A. Perio et al., Psychopharmacology, 1989, 87, 262-268). In this test a juvenile rat is placed in the home cage of an adult rat and the time spent by the adult rat in investigating the juvenile is measured in seconds (T1). The animals are then separated for 15 minutes and then the adult rat is again exposed to the same juvenile and the time of investigation during this second exposure is also measured (T2). In the case of normal animals, the recognition of the juvenile rat reduces the time of investigation (T2/T1<1) whereas when there is a memory impairment the T2/T1 ratio is $\geq 1$.

T-MAZE LEARNING TEST This test has been carried out according to the methodology described by P. Soubrié et al., in J. Pharmacol. (Paris), 1977,8,3,393-403 for the Y-maze test.

HOLEBOARD TEST (S. E. File et al., Pharmacol. Biochem. Behav., 1985, 22, 941-44).

ASSESSMENT OF THE LESIONS

Intraseptal vincristine administration affords a rapid and significant decrease (from 60 to 70% within one week after the injection) of the cholinergic markers of the hippocampus (choline acetyltransferase (ChAT) and acetylcholine esterase (AChE)), as well as a degeneration of the medial septum neurons which reaches its maximum two weeks after the injection, and which is associated with a reduction of the cholinergic markers. Said degeneration seems to be irreversible as it is still present three months after vincristine injection and involves functional disorders. Among those functional alterations which result from vincristine administration, the major finding is a consistent and irreversible memory impairment (social memory test). Parallel assays have brought up i.a. a reduction of the explorative capabilities (T-maze learning test and hole-board test).

TREATMENT SCHEDULES

The effects of administering Compound A to the animals lesioned as above have been compared with those obtained by administering NGF.

Compound A is administered orally, 2 to 3 hours after vincristine injection, as a 1% carboxymethylcellulose suspension, 10 ml of suspension per kg of body weight. The controls receive the vehicle only. The treatment is chronic, once a day for 11 days. Compound A is administered at three different doses: 2.5 mg/kg, 5 mg/kg, and 10 mg/kg to groups of 8 animals each, and the animals are sacrificed 24 hours after the end of the treatment. On the contrary NGF is administered by intraventricular infusion, dissolved in artificial cerebrospinal fluid (ACSF) containing 0.01% rat albumin and gentamycin (1 ml/15 ml) according to the method described by W. Fisher et al., in Nature, 1987, 329 (6134), 65-8. NGF concentration in the solution is calculated in view of the selected diffusion flow rate ($0.44 \pm 0.02$ $\mu$l/h) so as to provide the animals (7 rats) with an overall amount of 0.105 $\mu$g, 1.05 $\mu$g, or 10.5 $\mu$g of NGF over two weeks of infusion. In the controls, NGF is replaced by a protein of similar molecular weight (about 130.000) which has no neurotrophic activity: cytochrome C. Two weeks after the lesions have been placed and the treatment has begun, the animals are sacrificed. One group of sacrificed animals is perfused for histoenzymatic determination of AChE, the other animals are on the other hand employed for the assay of ChAT activity in both hippocampus and septum.

RESULTS

Morphological observations

In the lesioned, untreated, animals no dark precipitate is seen while the hippocampal buddings observed in the animals treated with 5 mg/kg of Compound A are quite similar to those seen in normal animals. These results are analogous to those obtained in the NGF-treated animals.

Biochemical evaluation

The lesions provoke a marked decrease of ChAT activity in the hippocampus whose extent is reduced in a dose-dependent manner by Compound A, up to a complete recovery with the dose of 10 mg/kg. Analogous results are obtained in the NGF perfused animals. Mose particularly the obtained results are summariaed in the following table II

TABLE II

| | ChAT activity (pmols/mg/mn) |
|---|---|
| non-lesioned normal animals | 277 ± 13 |
| lesioned controls | 115 ± 18 |
| NGF 0.105 $\mu$g/rat/2 weeks | 168 ± 27 |
| NGF 1.05 $\mu$g/rat/2 weeks | 336 ± 28 |
| NGF 10.5 $\mu$g/rat/2 weeks | 293 ± 10 |
| non-lesioned normal animals | 242 ± 19 |
| lesioned controls | 97 ± 18 |
| Compounds A 2.5 mg/kg/day | 164 ± 42 |
| Compounds A 5 mg/kg/day | 204 ± 24 |
| Compounds A 10 mg/kg/day | 242 ± 27 |

In the septum, the lesions afford reduction of ChAT activity which is restored, in a dose-dependent manner, by the administration of Compound A. In the NGF-treated animals the results are not significative probably because in addition to the septal necrosis produced by the vicristine injection, an additional necrosis associated with the implantation of a cannula in a ventricle near the septum develops.

BEHAVIOURAL OBSERVATIONS

Social memory test

The vincristine lesioned animals show alterations in social memory which seem to be irreversible (said alterations are still present 50 days after vincristine injection). Compound A has been tested at the dose of 10 mg/kg per os in comparison with NGF at the dose of 10.5 $\mu$g and the test has been performed on day 7 from placement of the lesions.

In both cases a very important protecting effect has been elicited with a T2/T1 ratio of between 0.6 and 0.7.

T-maze test

The results obtained in the lesioned, untreated, animals show an alteration in the exploratory activity which is however restored to the normal level by administration of 10 mg/kg of Compound A.

This test has been carried out in blind, 7 days after the end of the treatment.

Holeboard test

In the controls, most of the animals (6 rats) completely lost their exploratory capacity, while only two rats showed an exploratory hyperactivity. Treatment with Compound A at the dose of 10 mg/kg leads to a normalisation of the explorative behaviour compared with the average results obtained with unlesioned animals.

Said test too has been carried out in blind, 11 days after the end of the treatment.

To further confirm the efficacy of the compounds of formula (I) as neurotrophic agents an additional test has been carried out in vivo. This test which is analogous to that described by P. De Koning et al. in Journal of the Neurological Sciences, 1986, 74, 237–246, evaluates the return of motor function after peripheral nerve damage and more particularly after sciatic nerve crush.

Male Sprague-Dawley rats, weighing 175–200 g (Charles River) were kept in plastic cages in conditioned rooms (22°+1° C., 40–70% humidity), on a 12 h dark-light cycle with free access to food and water.

A crush lesion was placed in the sciatic nerve of the rats anaesthetized with ether. The procedure used to provoke the crush lesion was similar to that described by P. De Koning et al.. More particularly the skin of the anaesthetized rats was cut on the external side of the left hindpaw and muscle lateralis and muscle biceps femoris were separated. The sciatic nerve was elevated over the muscles, forceps (1.5 mm thick) were placed 10 mm distal from the point of emergence and closed maximally for 90 seconds. The nerve was then put in the same place and the skin sutured.

Volumes of 10 ml/kg of 1% carboxymethylcellulose (CMC) or of a suspension of compound A in 1% CMC were administered p.o 1 hour after the lesion and then daily for 16 days, 1 hour after the evalutation of the motor function. Return of motor function was evaluated daily beginning on day 10 after the lesion. The results were scored as follows:

2: no recovery of the injured paw
1.5: reappearing of toes motor function without return of the "clutch" reflex
1: reappearing of the "clutch" reflex
0: return of the "clutch" reflex, normal walk and normal respective positioning of the toes.

The results obtained are summarized in the following Table. Difference in scores between the groups were statistically compared by means of an ANOVA test and of a Dunnet test.

TABLE

| Compound Dose | No. of Animals | Motor function return Day after the lesion - Scores ± ESM | | | | |
|---|---|---|---|---|---|---|
| | | 13 | 14 | 15 | 16 | 17 |
| 1% CMC | 34 | 1.85 ±0.07 | 1.38 ±0.09 | 1.03 ±0.08 | 0.47 ±0.08 | 0.08 ±0.05 |
| Compound A 10 mg/kg in 1% CMC | 34 | 1.60* ±0.01 | 1.26 ±0.08 | 0.59** ±0.08 | 0.32 ±0.08 | 0.05 ±0.04 |

*$P<0.05$ v. control, Dunnest test
**$P<0.01$ v control, Dunnest test

The above results, which show the effectiveness of compound A in speeding up return of motor function after sciatic nerve crush further confirm the utility of the compounds of formula (I) in the treatment of peripheral neuropathies. In the light of the results obtained in the above models, the use of the compounds of formula (I) as well as of their pharmaceutically acceptable salts in the treatment and/or prevention of diseases involving neuronal degeneration can be envisaged. More particularly the compounds of formula (I) as well as their pharmaceutically acceptable salts can be employed mainly in the following indications: memory impairment, vascular dementia, post-encephalitic disorders, post-apoplectic disorders, post-traumatic syndrome caused by injury to the head, degenerative modifications associated with cerebral anoxia, Alzheimer's disease, senile dementia, sub-cortical dementia, such as Huntington's chorea and Parkinson's disease, AIDS dementia, neuropathies caused by lesions or degeneration of sympaphetic or sensory nerves and cerebral diseases such as cerebral oedema and spinocerebellar degenerations.

The compounds of formula (I) or their pharmaceutically acceptable acid addition salts may advantageously be administered orally, parenterally, sublingually or transdermally. The amount of active principle to be administered in the treatment of cerebral and neuronal diseases according to the method of the present invention will vary, as usually depending on the nature and conditions of the disease to be treated as well as on the weight of the patients.

Generally speaking, preferred unit dosage forms will contain from 2 to 300 mg, preferably from 5 to 150 mg, comprised by way of example between 5 and 50 mg, e.g. 5, 10, 20, 30, 40, and 50 mg, of active principle. Said unit doses are generally administered one or more times a day, e.g. 2, 3, 4, or 5 times a day, preferably from 1 to 3 times a day, the overall daily dosage in humans being from 2 to 900 mg, typically from 3 to 500 mg, more advantageously from 10 to 300 mg.

For a therapeutic or preventive treatment according to the present invention, the compounds of formula (I) and their pharmaceutically acceptable acid addition salts are preferably formulated in pharmaceutical compositions.

The pharmaceutical compositions of the present invention contain an amount of at least one compound selected from the compounds of formula (I) and their pharmaceutically acceptable addition salts which is effective for the treatment or the prevention of cerebral and neuronal diseases, in admixture with a pharmaceutically inert carrier.

As for the oral or sublingual administration, in particular tablets, optionally sugar-coated, capsules, optionally containing a slow-release formulation, drops or liposomes may be used. As for the intravenous, subcutaneous, or intramuscular administration, sterile or sterilisable solutions are employed, while conventional patches for transdermal administration can be utilised.

The pharmaceutical compositions according to the present invention can be prepared by conventional techniques such as those described in EP-101381 or in Remington's Pharmaceutical Sciences, 18<sup>th</sup> Ed, mack Publishing Company. The activity principle may be incorporated to excipients usually employed in said pharmaceutical compositions, such as talc, arabic gum, lactose, starch, magnesium stearate, aqueous or non aqueous vehicles, animal or vegetable fats, paraffins, glycols, wetting, dispersing, emulsifying and preservative agents, etc.

The pharmaceutical compositions according to the invention may advantageously contain a compound of formula (I) or a pharmaceutically acceptable salt thereof in association with one or more other medicaments, known or actually employed for the same therapeutic or prophylactic indications.

We claim:

1. A method of treating neuronal degenerative processes which comprises administering to a mammal in need thereof, a compound of formula (I)

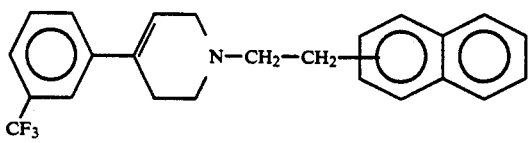

or a pharmaceutically acceptable salt thereof, wherein said compound is administered in an amount effective to treat said neuronal degeneration.

2. The method of claim 1 for the treatment of memory impairments, vascular demential, post-encephalitic disorders, post-apoplectic disorders, post-traumatic syndrome caused by brain injury, cerebral anoxic diseases, Alzheimer's disease, senile demential, subcortical demential including Huntington's chorea and Parkinson's disease, AIDS dementia, neuropathies provoked by sympathetic or sensory nerve necrosis or lesions, cerebral oedema or spinocerebellar degenerations.

3. The method of claim 2 for the treatment of vascular demential, senile demential or Alzheimer's disease.

4. The method of claim 1 wherein the compound of formula (I) is 1-[2-(2-naphthyl)-ethyl]-4-(3-trifluoromethylphenyl)-1,2,3,6-tetrahydropyridine or a pharmaceutically acceptable acid addition salt thereof.

* * * * *

UNITED STATES PATENT AND TRADEMARK OFFICE
CERTIFICATE OF CORRECTION

PATENT NO. : 5,270,320

DATED : December 14, 1993

INVENTOR(S) : Francoise X. Coude, et al

It is certified that error appears in the above-identified patent and that said Letters Patent is hereby corrected as shown below:

On title page, between items [22] and [30] add the following:

--Related U.S. Application Data
Continuation-in-part of application serial no. 07/703,835 filed on May 21, 1991, now U.S. Patent No. 5,229,389.--

In column 1, immediately after the title, please insert:

--The present invention is a continuation-in-part of U.S. Application Serial No. 07/703,835 filed on May 21, 1991, which has now issued as U.S. Patent No. 5,229,389.--

Signed and Sealed this

Fifteenth Day of July, 1997

*Attest:*

BRUCE LEHMAN

*Attesting Officer*  *Commissioner of Patents and Trademarks*